United States Patent [19]

Price

[11] 4,070,451
[45] Jan. 24, 1978

[54] HOOF CARE EMULSION OR CREAM

[76] Inventor: Howard Price, 270-11V Grand Central Parkway, Floral Park, N.Y. 11005

[21] Appl. No.: 738,147

[22] Filed: Nov. 2, 1976

[51] Int. Cl.² ............................................. A61K 7/04
[52] U.S. Cl. ...................................................... 424/61
[58] Field of Search .................................. 424/61, 177

[56] References Cited

U.S. PATENT DOCUMENTS

| 3,887,702 | 6/1975 | Baldwin | 424/61 |
| 3,917,824 | 11/1975 | Camble | 424/177 |

OTHER PUBLICATIONS

Sagarin, Cosmetics Science & Technology (1957) pp. 709–711.

Miller et al., Encyclopedia of Animal Care (1962) p. 343.

Primary Examiner—Sam Rosen
Attorney, Agent, or Firm—Bauer, Amer & King

[57] ABSTRACT

There is provided an improved hoof-treatment composition comprising basically and essentially an aqueous emulsion of a relatively material amount of each of a glycerol stearate, lanolin wax, lanolin alcohols, stearic acid, mineral oil, and paraffin, together with a relatively lesser amount of each of a polysorbate, sodium lauryl sulfate, a hydrolyzed animal protein, and imidazolinidyl urea. Glycerine, petrolatum, and beeswax, each in a relatively material amount, may also be included with advantage. Desirably, one or more of a lower alkyl p-hydroxy-benzoate, a coloring ingredient, a perfume ingredient, and vitamin E, each in a relatively lesser amount, may be present.

10 Claims, No Drawings

HOOF CARE EMULSION OR CREAM

BACKGROUND OF THE INVENTION

This invention relates to compositions for the treatment of keratinous tissues and is particularly concerned with the provision of an improved composition that can be applied to animal hooves to maintain the same in a supple and healthy state.

In the care of animals such as cattle, horses, and the like, an important factor is the maintenance of the animal's hooves in proper condition. It is particularly desirable in this regard to prevent the hooves from drying out and becoming brittle so as to avoid chipping, cracking, and/or flaking of the same. This requirement holds true especially for horses, whose hooves are generally subjected to working and other conditions that cause and/or tend to aggravate such drying out.

Various preparations have been proposed heretofore to provide such hoof care. Some of such preparations possess a more or less unpleasant odor which renders their use objectionable; others are messy to apply or are otherwise undesirable in use. Thus, for one reason or another, these prior preparations leave more than something to be desired in their general usefulness.

SUMMARY OF THE INVENTION

It has now been found that the disadvantages of such prior preparations can be substantially mitigated or largely overcome by means of the present invention, which provides an improved composition for the treatment of animal hooves, nails, and similar keratinous tissues in order to render and maintain the same healthfully supple and pliant.

According to the invention, such improved hoof-treatment composition comprises basically and essentially an aqueous emulsion of a relatively material amount of each of a glycerol stearate, lanolin wax, lanolin alcohols, stearic acid, mineral oil, and paraffin, together with a relatively lesser amount of each of a polysorbate, sodium lauryl sulfate, a hydrolyzed animal protein, and imidazolinidyl urea. Such ingredients provide a formulation that is, quite unexpectedly, substantially superior to existing and previously proposed preparations in attaining the desired results.

Glycerine, petrolatum, and beeswax, each in a relatively material amount, may also be included with advantage. Desirably, one or more of a lower alkyl p-hydroxybenzoate, a coloring ingredient, a perfume ingredient, and vitamin E, each in a relatively lesser amount, may be present.

DESCRIPTION OF THE PREFERRED EMBODIMENTS

As set forth above, the composition of the invention comprises an aqueous emulsion containing the indicated ingredients. Those ingredients that are essential for accomplishing the desired results are present in parts by weight within the following ranges:

| | |
|---|---|
| Glycerol stearate | 11.0 – 13.0 |
| Lanolin wax | 5.0 – 7.0 |
| Lanolin alcohols | 5.6 – 6.5 |
| Stearic acid | 4.0 – 6.0 |
| Mineral oil | 4.5 – 6.0 |
| Paraffin | 1.5 – 3.5 |
| Polysorbate | 0.5 – 2.0 |
| Sodium lauryl sulfate | 0.4 – 0.6 |
| Hydrolyzed animal protein | 0.2 – 0.5 |

-continued

| | |
|---|---|
| Imidazolinidyl urea | 0.1 – 0.25 |

Of these ingredients, the glycerol stearate, the lanolin wax, the lanolin alcohols, the stearic acid, the mineral oil, and the paraffin basically constitute the oil phase of the emulsion. Their primary purpose is to provide the means to prevent or to counteract the drying-out of hooves or nails and thereby to avoid the undesirable and potentially harmful or injurious cracking or chipping of the same. In doing so, these oil-phase ingredients act as moisturizing oils or emollients and thus effectively maintain the hooves or nails in their natural, supple condition. In place of glycerol stearate, an equivalent ester such as glycerol palmitate may be utilized.

It is to be particularly noted in this regard that these oil-phase ingredients are all natural or naturally derived materials. As such, they introduce no harmful substances into the hoof-treatment composition and complement the natural condition of the hooves or nails themselves.

Satisfactory results are obtained by use of a composition containing these ingredients within the respective indicated ranges. Any material variation in such respects renders the resulting composition less effective for the desired purpose.

The remaining ingredients, namely, the polysorbate, the sodium lauryl sulfate, the hydrolyzed animal protein and the imidazolinidyl urea are contained in the aqueous or water phase of the emulsion. The polysorbate and the sodium lauryl sulfate serve primarily as emulsifiers or surfactants in the formation of the emulsified composition. Other surfactants equivalent in effect to that of sodium lauryl sulfate may be employed in place of the latter, in part or in whole. The hydrolyzed animal protein and the imidazolinidyl urea assist in the proper maintenance of the hooves or nails and act, in this way, as nutritional agents. As with the oil-phase ingredients, the water-phase ingredients provide satisfactory results when they are utilized within the respective indicated ranges.

Advantageously, the present composition also includes the following ingredients in parts by weight within the specified ranges:

| | |
|---|---|
| Glycerine | 4.0 – 7.0 |
| Petrolatum | 3.0 – 5.0 |
| Beeswax | 1.5 – 2.5 |

The petrolatum and the beeswax comprise part of the oil phase of the emulsion and assist the emollient effect of such phase. The glycerine is contained in the water phase and serves to enhance the softening effect of the instant preparation when it is applied to a hoof. Again, satisfactory results are obtained when these additional ingredients are employed within the ranges given above. These further ingredients are all also natural or naturally derived products.

One or more of the following ingredients, in parts by weight within the indicated ranges, may desirably be present:

| | |
|---|---|
| Lower alkyl p-hydroxybenzoate | 0 – 0.5 |
| Coloring ingredient (including any solvent) | 0 – 2.0 |
| Perfume ingredient | 0 – 1.9 |

-continued

| | |
|---|---|
| Vitamin E | 0 – 0.05 |

The lower alkyl p-hydroxybenzoate serves to prevent bacterial spoilage; and more than one alkyl p-hydroxybenzoate may be employed. Generally speaking, the alkyl group in such compound contains 1 to 4 carbon atoms. Any suitable coloring ingredient may be utilized so long as it is chemically and esthetically compatible with the remainder of the composition; a typical example comprises F, D & C Blue #1, which is soluble in the water phase and which is employed as an aqueous solution of suitable dilute concentration. A similar requirement applies to the perfume ingredient, which may comprise any suitable perfume oil, whether naturally derived and/or synthetically prepared. The vitamin E services as an anitoxidant and to fortify the hoof tissues. As before, the use of these ingredients within the stated ranges provides satisfactory results.

A preferred basic formulation comprises the following ingredients, other than water, in essentially the indicated parts by weight:

| | |
|---|---|
| Glycerol stearate (Arlacel 165) | 12.0 |
| Lanolin wax (Lanfrax) | 6.0 |
| Lanolin alcohols (Amerchol L-101) | 6.0 |
| Stearic acid | 5.0 |
| Mineral oil (mineral oil 65/75) | 5.0 |
| Paraffin | 2.0 |
| Polysorbate (polysorbate 20) | 1.0 |
| Sodium lauryl sulfate | 0.5 |
| Hydrolyzed animal protein (Crotein SPO) | 0.3 |
| Imidazolinidyl urea (Gerinall 115) | 0.125 |
| Methyl p-hydroxybenzoate (methyl paraben - Tegosept M) | 0.125 |
| Propyl p-hydroxybenzoate (propyl paraben - Tegosept P) | 0.05 |

The water used is preferably deionized. Commercial stearic acid, which comprises about 50% stearic acid, about 45% palmitic acid, and about 5 oleic acid, forms the stearic acid component. Polysorbate 20 is essentially polyoxyethylene sorbitan monolaurate. The hydrolyzed animal protein is derived from collagen; it comprises a collagen hydrolyzate.

Advantageously, this preferred basic information includes the following further ingredients in essentially the indicated parts by weight:

| | |
|---|---|
| Glycerine | 5.0 |
| Petrolatum | 4.0 |
| Beeswax | 2.0 |
| F, D & C Blue #1 (dilute aqueous solution) | 1.2 |
| Perfume oil | 0.3 |
| Vitamin E | 0.01 |

The petrolatum has a consistency similar to that of petroleum jelly. The beeswax is a yellow beeswax although other grades may be equally employed. The F, D & C Blue #1 is utilized as a suitable water solution of appropriate dilution. The perfume oil comprises a naturally derived or synthetically prepared oil or blend of oils.

The present composition is desirably produced by separately preparing the oil phase and the water phase and then combining such two phases to form the desired emulsion or cream. The ingredients of the oil phase are placed at about 0° C. in a heating vessel preferably in the following order: the lanolin alcohols, the beeswax (if used), the glycerol stearate, the petrolatum (if used), the paraffin, the stearic acid, the lanolin wax, the mineral oil, and the propyl paraben (if used). Once so mixed, such ingredients are slowly heated with stirring to a temperature of 72 to 77° C., preferably about 75° C. The vitamin E (if used) is added as convenient.

In the preparation of the water phase, the water is placed in a separate heating vessel at ambient temperature. To such water are then added, preferably in the indicated order, the glycerine (if used), the sodium lauryl sulfate, the hydrolyzed animal protein, the methyl paraben (if used), and the imidazolinidyl urea. The resulting mixture is then slowly heated, with stirring, to a temperature of 72° to 77° C., preferably about 75° C. The polysorbate is added as convenient.

With the oil phase and the water phase both at or about the same top temperature, the heated water phase is added to or poured into the heated oil phase. The resulting mixture is allowed to gradually cool while it is being strongly stirred so that the desired emulsion or cream is formed. At a temperature of 50° to 60° C., preferably about 55° C., the coloring ingredient (if used) is added, stirring being continued. When the emulsion reaches a temperature of 40° to 50° C., the perfume ingredient (if used) is added. Pouring of the final emulsion into suitable containers such as jars takes place at a temperature of 40° to 44° C., usually around 42° C.

In the use of the present composition, the hoof or hooves to be treated are first cleaned and freed from any dirt or grit. An appropriate amount of the composition is then applied to and massaged into the hoof, particularly directly into the hoof wall, the hard sole, the frog, and especially the coronet. For best results, the composition should be utilized daily. Application of the composition may readily be done by hand, no medium such as rags, gloves, and paint brushes being necessary, without irritation or other injury to the skin.

As will be apparent, there is thus provided a hoof-treating composition which is easy to apply and which readily maintains a horse's hooves supple and healthy. Such preparation is especially beneficial in view of its particular content of moisturizing oils and its inclusion of protein and vitamin substances. Moreover, this formulation avoids the unpleasant odors and messy characteristics of ordinary hoof compounds.

Although the specific formulation set forth above is preferred, other compositions falling within the above-indicated range limits also provide the surprising benefits of the present invention.

What is claimed is:

1. A composition for the treatment of keratinous tissues which comprises an aqueous emulsion containing the following ingredients in parts by weight:

| | |
|---|---|
| Glycerol stearate | 11.0 – 13.0 |
| Lanolin wax | 5.0 – 7.0 |
| Lanolin alcohols | 5.6 – 6.5 |
| Stearic acid | 4.0 – 6.0 |
| Mineral oil | 4.5 – 6.0 |
| Paraffin | 1.5 – 3.5 |
| Polysorbate | 0.5 – 2.0 |
| Sodium lauryl sulfate | 0.4 – 0.6 |
| Hydrolyzed animal protein | 0.2 – 0.5 |
| Imidazolinidyl urea | 0.1 – 0.25 |

2. A composition according to claim 1, which also includes 0 to 0.5 parts by weight of one or more lower alkyl p-hydroxybenzoates.

3. A compositon for the treatment of keratinous tissues which comprises an aqueous emulsion containing the following ingredients in essentially the indicated parts by weight:

| | |
|---|---|
| Glycerol stearate | 12.0 |
| Lanolin wax | 6.0 |
| Lanolin alcohols | 6.0 |
| Stearic acid | 5.0 |
| Mineral oil | 5.0 |
| Paraffin | 2.0 |
| Polysorbate | 1.0 |
| Sodium lauryl sulfate | 0.5 |
| Hydrolyzed animal protein | 0.3 |
| Imidazolinidyl urea | 0.125 |
| Methyl p-hydroxybenzoate | 0.125 |
| Propyl p-hydroxybenzoate | 0.05 |

4. A composition according to claim 1, which also includes in parts by weight:

| | |
|---|---|
| Glycerine | 4.0 – 7.0 |
| Petrolatum | 3.0 – 5.0 |
| Beeswax | 1.5 – 2.5 |

5. A composition according to claim 4, which further includes 0 to 0.5 parts by weight of one or more lower alkyl p-hydroxybenzoates.

6. A composition according to claim 4, which further includes 0 to 2.0 parts by weight of a compatible coloring ingredient.

7. A composition according to claim 4, which further includes 0 to 1.9 parts by weight of a perfume ingredient.

8. A composition according to claim 4, which further includes 0 to 0.05 parts by weight of vitamin E.

9. A composition according to claim 3, which also includes in essentially the indicated parts by weight:

| | |
|---|---|
| Glycerine | 5.0 |
| Petrolatum | 4.0 |
| Beeswax | 2.0 |
| F, D & C Blue #1 | 1.2 |
| Perfume oil | 0.3 |
| Vitamin E | 0.01 |

10. A method of treating an animal hoof, which comprises applying to the hoof a composition according to claim 1 in an amount effective to prevent drying-out of such hoof, massaging such applying and massaging steps as necessary to maintain the hoof in the desired condition.

* * * * *

UNITED STATES PATENT OFFICE
CERTIFICATE OF CORRECTION

Patent No. 4,070,451　　　　　　　　　　Dated January 24, 1978

Inventor(s) Howard Price

It is certified that error appears in the above-identified patent and that said Letters Patent are hereby corrected as shown below:

Claim 10, line 4, after first instance of "massaging" insert -- such applied composition into the hoof, and repeating --.

Signed and Sealed this

Second Day of May 1978

[SEAL]

Attest:

RUTH C. MASON  
Attesting Officer

LUTRELLE F. PARKER  
Acting Commissioner of Patents and Trademarks